United States Patent [19]

Virgilio

[11] Patent Number: 5,661,104
[45] Date of Patent: Aug. 26, 1997

[54] PRESERVATIVE COMPOSITIONS FOR USE IN AQUEOUS SYSTEMS

[75] Inventor: Joseph A. Virgilio, Wayne, N.J.

[73] Assignee: Givaudan-Roure (International) SA, Vernier-Geneve, Switzerland

[21] Appl. No.: 661,926

[22] Filed: Jun. 11, 1996

[51] Int. Cl.[6] .................................................. A01N 33/18
[52] U.S. Cl. ............................................ 504/150; 514/741
[58] Field of Search ............................. 514/741; 504/150

[56] References Cited

U.S. PATENT DOCUMENTS

| | | | |
|---|---|---|---|
| 2,876,160 | 3/1959 | Schoch et al. | 167/82 |
| 3,535,423 | 10/1970 | Ordas | 424/176 |
| 3,629,465 | 12/1971 | Manowitz et al. | 424/349 |
| 3,871,860 | 3/1975 | Manowitz et al. | 71/67 |
| 4,755,397 | 7/1988 | Eden et al. | 427/213.3 |
| 4,963,179 | 10/1990 | Purzycki et al. | 71/67 |
| 5,122,301 | 6/1992 | McCoy et al. | 252/384 |

OTHER PUBLICATIONS

EPA "Inert Ingredients in Pesticide Products"; Policy statement Federal Register, vol. 52, No. 77, 13305–13309 (1987).

*Primary Examiner*—Allen J. Robinson
*Attorney, Agent, or Firm*—George W. Johnston; Ellen Ciambrone Coletti; Mark E. Waddell

[57] ABSTRACT

The use of novel compositions for preserving aqueous systems normally subject to spoilage is disclosed. The compositions incorporate an antimicrobial agent into an inert and biodegradable carrier. The resulting compositions are stable, active, non-toxic, non-corrosive, biodegradable, compatible with ecosystems while having a flash point above 200° F. and a pleasant odor.

8 Claims, No Drawings

PRESERVATIVE COMPOSITIONS FOR USE IN AQUEOUS SYSTEMS

FIELD OF THE INVENTION

The present invention relates to compositions and processes for preserving aqueous systems against the deleterious action of bacteria, fungi, and algae.

SUMMARY

The present invention provides a novel means for the safe handling of β-bromo-β-nitrostyrene (BNS) by meeting desirable physical, chemical, environmental, and animal toxicological criteria. The present invention provides a product containing an antimicrobial agent in benzyl esters of $C_{2-4}$ carboxylic acids as inert and biodegradable carriers. The resulting compositions are stable, active; non-toxic, non-corrosive, biodegradable, and compatible with ecosystems while having a flash point above 200° F. and a pleasant odor.

The present invention also encompasses processes for manufacturing products containing from about 5% to about 40% BNS.

BACKGROUND

It is well known that various aqueous systems containing metabolizable components, either in trace or major quantities, are normally susceptible to attack and degradation by microorganisms. Examples of such compositions are cutting oils; cosmetics, such as lotions and creams; fuel oil; textile emulsions; latex emulsions and paints; starch-based adhesives; industrial cooling water; emulsion waxes; water used in pulp and paper manufacturing (so-called "process" water, e.g., "white water"); and flood water used in secondary oil recovery methods.

A number of problems and limitations have recently faced those in the art seeking to provide effective antimicrobial preservatives for such aqueous systems. These problems involve concerns about worker exposure and environmental impact. Many current preservatives are effective because they are toxic to microorganisms at low concentrations, e.g., about 100 parts per million (ppm). Human exposure to such preservatives in the parts per million range does not normally pose a health risk. The pure product, however, may pose an unacceptable risk to workers who may be exposed to the pure concentrated material on a daily basis, thereby requiring them to protect themselves from accidental inhalation or accidental skin exposure. A stable, non-hazardous formulation is therefore essential.

One method of keeping the concentration of such antimicrobial agents to an acceptable handling level involves using diluents. Diluents are also desirable to assist in delivering the antimicrobial agents to the medium being preserved. The diluents must, of course, meet certain criteria. For example, they must be compatible with a particular antimicrobial agent and with the medium in which the antimicrobial agent is to be used. They should not be highly flammable nor be toxic, thereby resulting in very few diluents satisfying these criteria at an acceptable price.

More recently, pressures concerning the toxicity of the diluent and its compatibility with the environment have resulted in restricting the number of acceptable diluents available for selection. It is expected that even fewer diluents or carriers will be acceptable in the future. There is a need in the industry to find a diluent or a carrier that meets the following criteria:

The diluent must be compatible with the antimicrobial agent and should not diminish or destroy its antimicrobial activity.

The final product must have a flash point greater than 150° F. in order to avoid dangers due to flammability.

The system must work in the intended medium.

It should not be on List 1 or List 2 of the United States Environmental Protection Agency's (EPA) "Inert Ingredients in Pesticide Products; Policy Statement." Lists 1 and 2 cover inert ingredients of extreme toxicological concern and potential toxicological concern, respectively.

The system must be economically competitive, i.e., it must not be so expensive that the system cannot compete in the market.

The diluent or carrier system should be either odorless or have a pleasant odor.

The antimicrobial agent should be quite soluble in the diluent.

Currently, the BNS product is a blend of Amsco Solv® F (Stoddard solvent) with and without N,N-dimethylformamide (DMF) and is believed to be the only non-oxidizing biocide on the market with a flammable warning label. Amsco Solv® F is 70% heavy aromatic hydrocarbons and 30% aliphatic hydrocarbons. The mixture of Amsco Solv® F and DMF has several undesirable characteristics. Both solvents have low boiling points and flash points: Amsco Solv® F (bp 178°–214° C.; FP 61° C.) and DMF (bp 153° C.; FP 58° C.). The Amsco Solv® F. and DMF blend also has an very undesirable odor, which has caused customers to discontinue the product.

Additionally, DMF has many undesirable properties, including causing skin irritation, stomach pains, vomiting, diarrhea, nausea, dizziness and headaches in humans. Acute effects of exposure to DMF may be caused by inhalation, ingestion, or skin absorption. Vapor or mist from DMF is irritating to the mucous membranes and upper respiratory tract. Dimethylformamide may also cause testicular cancer. Its use in pulp and paper manufacturing has all but ceased in the United States because it is on EPA's List 1, i.e., inert ingredients of extreme toxicological concern. Further, the oral $LD_{50}$ (rats) is 2.8 g/kg and the dermal $LD_{50}$ (rabbits) is 4720 mg/kg. The 6-hour inhalation ALC (rats) is 5000 ppm.

Although, for certain applications, a solid carrier system for BNS has been acceptable, in most instances a solvent system with desirable physical, chemical, environmental, and toxicological properties is needed. The present invention overcomes the disadvantages of prior compositions by providing compositions displaying the desirable characteristics outlined above.

DETAILED DESCRIPTION

Benzyl acetate occurs naturally in about a dozen essential oils, including jasmin, hyacinth, and gardenia. It has been in public use since the 1900's. Benzyl acetate has a long history of use in the flavor and fragrance industries. Benzyl acetate was given GRAS status by FEMA in 1965 and is approved by the FDA as a direct food additive (21 CFR 172.515).

Biological Data Benzyl Acetate

Acute toxicity. The acute oral $LD_{50}$ in rats was reported as 2.49 g/kg by Jenner, Hagan, Taylor, Cook & Fitzhugh (1964) and as 3.69 g/kg by Boyd & Kuizenga (1945). The $LD_{50}$ by dermal application was reported as >5 g/kg in the rabbit (Moreno, 1972).

Human testing. A maximization test (Kligman, 1966) was carried out on 25 volunteers. The material was tested at a concentration of 8% in petrolatum and produced no reactions (Greif, 1967).

Metabolism. The esters of benzyl alcohol, e.g., acetate, benzoate, cinnamate, and hydrocinnamate, are rapidly hydrolyzed in vivo to benzyl alcohol, which is then oxidized to benzoic acid and excreted as hippuric acid (Williams, 1959).

The properties outlined above allow the preparation of an antimicrobial composition of BNS in benzyl acetate, which is a biodegradable, inert, toxicologically safe, having a flash point above 200° F., and a pleasant odor.

Chemical stability tests were performed to determine if BNS was stable in benzyl acetate. The compositions were stored in closed, glass bottles at 50° C. for 28 days. The stability of BNS in benzyl acetate is demonstrated by the data presented in Table 3.

BNS was deactivated by reacting with methanol, ethanol, isopropyl alcohol, and t-butyl alcohol. Surprisingly, N,N-Dimethylformamide and N-methylpyrrolidinone were found to be incompatible as solvents with BNS.

The compositions have also been shown to be effective, in general, against a broad spectrum of microorganisms that attack the aqueous systems described herein. Samples of 30% and 40% BNS in benzyl acetate were evaluated in agar to obtain a minimum inhibitory concentration range of each sample against a series of bacteria, yeast, and molds. Pure BNS served as a control. The test was designed with small dilution increments to detect relatively minor differences in antimicrobial activity. Results indicated that the activity of the BNS samples in benzyl acetate compared favorably with the control. No significant differences in antimicrobial activity were detected. Benzyl acetate was tested alone and was found to be non-inhibitory against all microorganisms at 100 mcg/ml, the highest concentration of carrier tested, as depicted in Tables 1 and 2.

The microbial activity of BNS diluted with benzyl acetate is identical to an equivalent amount of the pure material and would, therefore, be useful as a preservative of aqueous systems as described in U.S. Pat. No. 3,629,465.

In view of the above, it will be seen that the objectives of the invention are achieved and provide an advantage over the previously described systems.

EXAMPLES

Samples of 30% and 40% BNS in benzyl acetate were evaluated for antimicrobial efficacy. The 30% and 40% BNS solutions were aged for 28 days at 50° C. The Minimum Inhibitory Concentration (MIC) is that concentration which completely inhibited the growth of the challenge inoculum. The test results are shown in Tables 1 and 2.

1. Product Preparation

Sodium acetate was added to a solution of 1,2-dibromo-2-nitroethylbenzene (U.S. Pat. No. 3,629,465) in toluene. The resulting mixture was refluxed for 4 hours. The solution was then cooled to room temperature and washed twice with a saturated salt solution. The resulting solution was heated to reflux with the azeotropic removal of water. After the toluene was dry, benzyl acetate was added and the toluene was removed under reduced pressure (30 mm Hg) at 50° C. to yield a solution of BNS in benzyl acetate.

Analysis of the solution by internal standard GC determined the concentration of BNS in benzyl acetate. Additional benzyl acetate was added to make the desired concentration of BNS in benzyl acetate, e.g., 30%, 35% or 40%.

In a similar manner, solutions were prepared using benzyl propionate, benzyl isobutyrate and benzyl butyrate in place of benzyl acetate. All were found stable.

2. Microbial Activity

Samples of 30% and 40% BNS in benzyl acetate were evaluated in agar to obtain a minimum inhibitory concentration range of each sample against a series of bacteria, yeast, and molds. Pure BNS served as a control. The test was designed with small dilution increments so that relatively minor differences in antimicrobial activity could be detected.

Results listed in the following tables indicate that the activity of the two samples compared favorably with the control. No significant differences in antimicrobial activity were detected.

TABLE 1

Bacteria

Minimum Inhibitory Concentration Range in mcg/ml BNS

| Sample | Staphylococcus aureus | Escherichia coli | Pseudomonas aeruginosa | Proteus vugaris | Bacillus subtilis |
|---|---|---|---|---|---|
| 30% BNS | >25 | 17.5–20.0 | 12.5–15.0 | 17.5–20.0 | 22.5–25.0 |
| 40% BNS | >25 | 15.0–17.5 | 10.0–12.5 | 15.0–17.5 | 20.0–22.5 |
| Pure BNS | >25 | 15.0–17.5 | 10.0–12.5 | 15.0–17.5 | 20.0–22.5 |

TABLE 2

Yeast and Molds

Minimum Inhibitory Concentration Range in mcg/ml BNS

| Sample | Candida albicans | Aspergillus niger | Aspergillus oryzae | Penicillium piscarium | Aureobasidium pullulans |
|---|---|---|---|---|---|
| 30% BNS | 15.0–17.5 | 7.5–10.0 | 12.5–15.0 | 7.5–10.0 | 2.5–5.0 |
| 40% BNS | 12.5–15.0 | 7.5–10.0 | 10.0–12.5 | 7.5–10.0 | 2.5–5.0 |
| Pure BNS | 12.5–15.0 | 10.0–12.5 | 10.0–12.5 | 7.5–10.0 | 2.5–5.0 |

In each range presented in Tables 1 and 2, no growth occurred at the higher concentration while the lower concentration was non-inhibitory. Benzyl acetate was tested alone and found to be non-inhibitory against all microorganisms at 100 mcg/ml, the highest concentration of carrier tested.

3. Stability and Compatibility

Samples of 30% and 40% BNS in benzyl acetate were placed in sealed brown glass bottles at a temperature of 50° C. and assayed for BNS content by GC with an internal standard over a 28 day period.

TABLE 3

Stability of BNS in Benzyl Acetate

| | Sample Concentration | | |
|---|---|---|---|
| | 30% | 35% | 40% |
| Initial | 30.70 | 34.80 | 39.61 |
| 7 Days | 30.78 | 35.10 | 39.66 |
| 14 Days | 30.80 | 35.21 | 39.80 |
| 21 Days | 30.70 | 35.10 | 39.60 |
| 28 Days | 30.81 | 35.11 | 39.64 |

Modification of the principles of the present invention are contemplated as would normally occur to one skilled in the art, and it is understood that no limitations of the scope of the present invention are intended.

We claim:

1. An antimicrobial composition for preserving aqueous systems comprising:

an antimicrobially effective amount of β-bromo-β-nitrostyrene and a benzyl ester of a $C_{2-4}$ carboxylic acid as an inert and biodegradable carrier.

2. The antimicrobial composition of claim 1 having from about 5 weight percent to about 40 weight percent β-bromo-β-nitrostyrene.

3. The antimicrobial composition of claim 1 wherein the inert and biodegradable carrier is selected from the group consisting of benzyl acetate, benzyl propionate, benzyl isobutyrate, and benzyl butyrate.

4. The antimicrobial composition of claim 3 having from about 5 weight percent to about 40 weight percent β-bromo-β-nitrostyrene.

5. The antimicrobial composition of claim 3 wherein the inert and biodegradable carrier is benzyl acetate.

6. The antimicrobial composition of claim 5 having from about 5 weight percent to about 40 weight percent β-bromo-β-nitrostyrene.

7. A process for forming an antimicrobial β-bromo-β-nitrostyrene in benzyl acetate solution, comprising:

(a) eliminating hydrogen bromide from 1,2-dibromo-2-nitroethylbenzene in toluene solution by treatment with sodium acetate, and (b) subsequently removing the toluene in the presence of benzyl acetate.

8. A process for forming an antimicrobial β-bromo-β-nitrostyrene in benzyl ester solution, comprising:

(a) eliminating hydrogen bromide from 1,2-dibromo-2-nitroethylbenzene in toluene solution, and (b) subsequently removing the toluene in the presence of a benzyl ester of a $C_{2-4}$-carboxylic acid.

* * * * *